(12) United States Patent
Holmqvist (10) Patent No.: US 9,440,030 B2
(45) Date of Patent: Sep. 13, 2016

(54) MEDICAMENT DELIVERY DEVICE

(75) Inventor: Anders Holmqvist, Värmdö (SE)

(73) Assignee: SHL Group AB, Nacka Strand (SE)

( * ) Notice: Subject to any disclaimer, the term of this patent is extended or adjusted under 35 U.S.C. 154(b) by 470 days.

(21) Appl. No.: 13/885,876

(22) PCT Filed: Nov. 18, 2011

(86) PCT No.: PCT/SE2011/051389
§ 371 (c)(1),
(2), (4) Date: May 16, 2013

(87) PCT Pub. No.: WO2012/067582
PCT Pub. Date: May 24, 2012

(65) Prior Publication Data
US 2013/0245558 A1    Sep. 19, 2013

Related U.S. Application Data

(60) Provisional application No. 61/415,065, filed on Nov. 18, 2010.

(30) Foreign Application Priority Data

Nov. 18, 2010 (SE) ...................................... 1051211

(51) Int. Cl.
*A61M 5/315* (2006.01)

(52) U.S. Cl.
CPC ..... *A61M 5/31551* (2013.01); *A61M 5/31525* (2013.01); *A61M 5/3155* (2013.01)

(58) Field of Classification Search
CPC .................... A61M 5/31551; A61M 5/31548; A61M 5/31525; A61M 5/3155; A61M 5/31565; A61M 5/3158
See application file for complete search history.

(56) References Cited

U.S. PATENT DOCUMENTS 5,514,097 A  *  5/1996  Knauer ........................ 604/136
8,276,583 B2    10/2012  Farieta et al.
(Continued)

FOREIGN PATENT DOCUMENTS

GB    2437924 A    11/2007
WO    03/077968 A2   9/2003
(Continued)

OTHER PUBLICATIONS

Sweden Patent Office, Int'l Search Report in PCT/SE2011/051389, Mar. 5, 2012.
Sweden Patent Office, Written Opinion in PCT/SE2011/051389, Mar. 5, 2012.

*Primary Examiner* — Nathan R Price
*Assistant Examiner* — Melissa A Snyder
(74) *Attorney, Agent, or Firm* — Piedmont Intellectual Property (57) ABSTRACT

The invention relates to a medicament delivery device comprising a housing arranged to receive a medicament container (20), a drive unit (25) arranged to act on a stopper (27) in said medicament container (20), which drive unit (25) comprises a torsion drive spring (50). A dose setting member (56) is operably connected to said drive unit (25) such that a manual turning of said dose setting member (56) causes a tensioning of said torsion drive spring (50). The device further comprises an activation mechanism (76) having an activation button (94) protruding through the distal end of the device, wherein said activation mechanism (76) is operably connected to said drive unit (25) such that actuation of said activation mechanism (76) causes a release of said drive unit (25) whereby a set dose of medicament is delivered.

11 Claims, 9 Drawing Sheets

(56) References Cited

U.S. PATENT DOCUMENTS

| | | | |
|---|---|---|---|
| 8,357,120 B2 * | 1/2013 | Moller et al. | 604/135 |
| 2010/0094214 A1 | 4/2010 | Abry et al. | |
| 2011/0098658 A1 * | 4/2011 | Enggaard et al. | 604/207 |
| 2011/0224622 A1 | 9/2011 | Karlsson | |
| 2011/0251553 A1 | 10/2011 | Ratjen et al. | |
| 2012/0029443 A1 | 2/2012 | Holmqvist | |

FOREIGN PATENT DOCUMENTS

| | | |
|---|---|---|
| WO | 2010/081489 A1 | 7/2010 |
| WO | 2010/139675 A1 | 12/2010 |
| WO | 2011/101349 A1 | 8/2011 |
| WO | 2011/101351 A1 | 8/2011 |
| WO | 2012/067583 A1 | 5/2012 |
| WO | 2012/067584 A1 | 5/2012 |

* cited by examiner

Fig. 7

MEDICAMENT DELIVERY DEVICE

TECHNICAL AREA

The present invention relates to a medicament delivery device and in particular a device provided with dose setting means.

BACKGROUND OF THE INVENTION

Many medicament delivery devices on the market are working with different types of drive means that are capable of, upon activation, acting on a stopper inside a medicament container for expelling a dose of medicament through a dose delivery member. The most common type of drive means that is used is a spirally wound compression spring.

A compressed compression spring may provide a force that is large enough to overcome the so called break loose force of the stopper, i.e. release the stopper from the inner wall of the medicament container and to be able to press the medicament in liquid form through a rather small passage in the delivery member, possibly within a predetermined time. Further, the spring at its full extension, which usually is not the full decompression, may provide a force that is large enough to complete the dose delivery, but it may also cause a breakage of the glass medicament container.

Some types of substances that are to be delivered have high viscosity, and because very small passages of the delivery member often are used, a rather large force is required. On the other hand the devices that utilize compression springs are often delivered to a user with the springs in compressed and a ready-to-use state because it is often difficult to tension the spring manually by a user and/or the device becomes very bulky if it would be provided with a spring tensioning mechanism.

Due to the pre-tension of the compression spring and in particular the very strong springs that are needed for high viscosity substances, there is a pronounced risk of breakage of the device when stored due to changes in the material, usually plastic, such as creeping and ageing. In that respect compression springs are not ideal.

In order to solve this, some devices utilize torsion springs that are tensioned by a user upon use of the device, i.e. the springs need not to be pre-tensioned, at least not to any larger degree. One device utilizing a torsion type of spring is disclosed in the document WO 2010/029043 where such a spring is wound around and connected to a drive member, capable of, upon activation, driving a drive nut such that a plunger rod, operably connected to the drive nut, is moved in a proximal direction whereby a dose of medicament is delivered through a medicament delivery member. The activation of the device and thus the release of the spring is performed by an actuation member that is positioned on a side surface of the housing of the device and slid in the proximal direction. However for some applications the position of the actuation member on a side surface is not ideal and for many users and also depending on where a preferred dose delivery site is positioned on the users body, it is preferred that the actuation member is positioned in a distal end area of the device.

UK 2437924 also relates to a torsion spring device having the activation button arranged on a side surface of the housing.

There is thus room for improvements of this type of medicament delivery device.

BRIEF DESCRIPTION OF THE INVENTION

The aim of the present invention is to remedy the drawbacks of the state of the art devices. This aim is obtained by a medicament delivery device according to the features of the independent patent claim. Preferable embodiments of the invention form the subject of the dependent patent claims.

According to a main aspect of the invention a medicament delivery device comprises a housing having at least one housing part, that said housing is arranged to receive a medicament container; a drive unit arranged to act on a stopper in said medicament container, which drive unit comprises a torsion drive spring; a dose setting member operably connected to said drive unit such that a manual turning of said dose setting member causes a tensioning of said torsion drive spring, wherein the device further comprises an activation mechanism having an activation button protruding through the distal end of the device, and said activation mechanism being operably connected to said drive unit such that actuation of said activation mechanism causes a release of said drive unit whereby a set dose of medicament is delivered.

According to another aspect of the invention said drive unit comprises an elongated plunger rod extending in the longitudinal direction of the device provided with threads on its outer surface and having a proximal end arranged to be in contact with said stopper; a drive nut provided with a central passage arranged with threads cooperating with the threads of said plunger rod, and that said drive unit comprises a drive member having a proximal end operably engaging said drive nut and drivably connected to said torsion drive spring such that, upon actuation of said activation mechanism, said drive nut as well as said drive member are rotated, whereby said plunger rod is moved in the proximal direction of the device.

According to another aspect of the invention said activation mechanism comprises actuation members attached to said activation button and extending in the proximal direction of the device, a drive nut lock member attached to said actuation members, which drive nut lock member is releasably engaging and locking said drive nut via cooperating locking members until said actuation button is moved in the proximal direction, whereby said drive nut is released.

According to a further aspect of the invention said drive nut and said drive member of said drive unit are operably connected via wedge-shaped ratchets, on the one hand enabling turning of said drive nut when said drive member is turned by said torsion drive spring upon activation, thereby driving said plunger rod for expelling a dose of medicament from said medicament container, and on the other hand such that said dose setting member is operably connected to said drive member such that manual operation of said dose setting member causes a turning of said drive member in relation to said drive nut for setting a dose of medicament to be delivered from said medicament container, which turning tensions said torsion drive spring.

According to yet another aspect of the invention the device further comprises a dose barrel rotatably arranged inside said housing, which dose barrel is operably connected to said dose setting member and wherein said dose barrel is arranged with indicia on its outer surface visible in a window in said housing, which indicia displays a set dose when said dose setting member is turned by a user.

According to yet a further aspect of the invention said dose barrel is arranged with threads on its outer surface, cooperating with corresponding threads on an inner surface of said housing.

According to another aspect of the invention said indicia is positioned spirally on the dose barrel.

According to yet another aspect of the invention said dose setting member and said drive member are axially movable in the distal direction against a force from a spring such that a displacement of said dose setting member in the distal direction causes said ratchets to move out of contact with each other admitting a resetting of a set dose.

According to a further aspect of the invention said housing comprises a distal part and a proximal part, wherein said proximal part is arranged to accommodate said medicament container, and wherein said housing parts are arranged with releasable attachment means.

According to yet another aspect of the invention it further comprises a guide member arranged to rotatably lock said plunger rod, and wherein said attachment means are arranged such as to act on and lock said guide member when said housing parts are attached to each other, and wherein, when said housing parts are disconnected from each other, said guide member and thus said plunger rod is free to rotate, whereby said plunger rod can be moved in the distal direction to its initial position when a new medicament container is to be used.

The advantages of the present invention are several. The use of proximally extending actuation members enables activation and release of the torsion drive spring also when the actuation button is placed in the distal end area of the device. This is an advantage for many users in that they are able to hold the device such that the activation button is operated by a thumb. If for instance the device is an injector and the preferred delivery site is the thigh, the belly or the arm, such a grip is preferred.

Also, the use of a drive member operably connected to the drive nut where the drive member is operably connected to said torsion drive spring provides a number of possibilities. One is that the drive member and the drive nut are locked together in one rotational direction, i.e. when a dose is to be delivered, and released from each other in the opposite rotational direction. This enables the drive member to be rotated by the dose setting mechanism for setting a desired dose without the drive nut being rotated. Further the rotation of the drive member causes a tensioning of the torsion drive spring. The device thus does not have to be stored with a pre-tensioned spring.

The use of a dose barrel that is threaded in relation to the housing and thus is moved also in the longitudinal direction, provides the advantage that a large number of indicia and/or larger size of the indicia is possible because the length that can be used is far longer than the mere circumference of the device. Thereby it is also possible to handle doses that require more than 360° turning of the dose setting member.

Further, the device is arranged with means for replacing a used medicament container with a new container in a simple and effective way where it is uncomplicated for a user to reset the plunger rod to its initial position.

These and other aspects of and advantages with the present invention will become apparent from the following detailed description and from the accompanying drawings.

BRIEF DESCRIPTION OF THE DRAWINGS

In the following detailed description of the invention, reference will be made to the accompanying drawings of which

DETAILED DESCRIPTION OF THE INVENTION

In the present application, when the term "distal part/end" is used, this refers to the part/end of the delivery device, or the parts/ends of the members thereof, which is/are located the furthest away from the medicament delivery site. Correspondingly, when the term "proximal part/end" is used, this refers to the part/end of the delivery device, or the parts/ends of the members thereof, which, is/are located closest to the medicament delivery site.

The exemplary embodiment of the medicament delivery device shown in the drawings comprises a generally tubular elongated distal housing part 10 having a proximal end provided with attachment means 12. The attachment means 12, in the embodiment shown as threads, are arranged to cooperate with corresponding attachment means 14, FIG. 3, on a proximal housing part 16 for releasable attachment of the housing parts. In this context it is to be understood that other types of attachment members may be used. Also the device may comprise other number of housing parts depending on application and manufacturing aspects.

The proximal housing part 16 is arranged with a proximal neck 18 having attachment members that are intended to cooperate with corresponding attachment members on a medicament delivery member (not shown) such as an injection needle, a mouth or nose piece, a nebulizing nozzle or the like. The proximal housing part 16 is further arranged to accommodate a medicament container 20 having a proximal neck portion 21 fitting into the neck 18 of the proximal housing part 16. The proximal housing part 16 is further arranged with windows or openings 22 through which the medicament container is visible, and if the container preferably is made of a transparent material, the content of the medicament container 20 is visible to a user. A protective cover 23 is releasably arranged to the proximal housing part.

Figure 1:
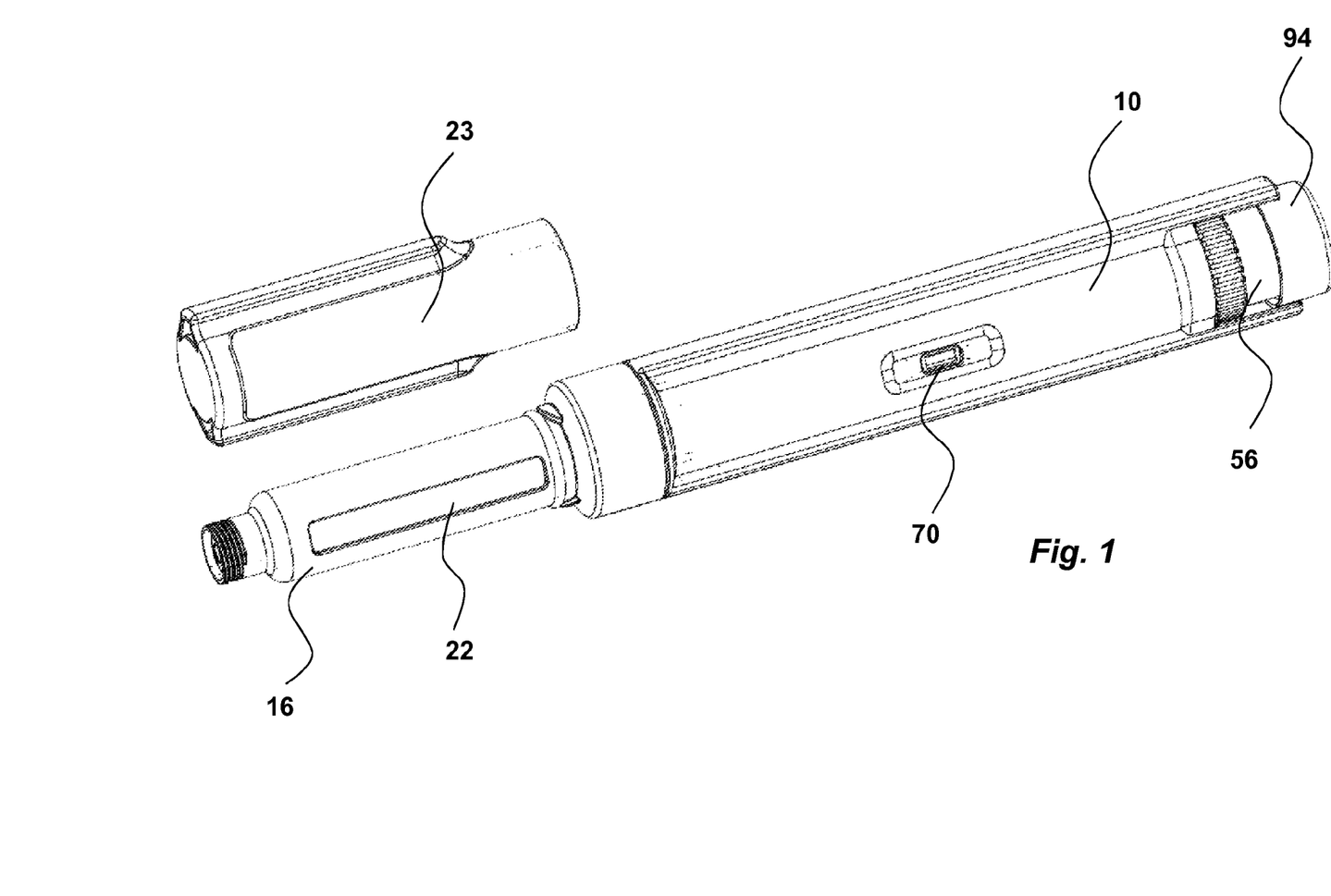
FIG. 1 is a perspective view of an exemplary embodiment of a medicament delivery device according to the present invention.
Figure 2:
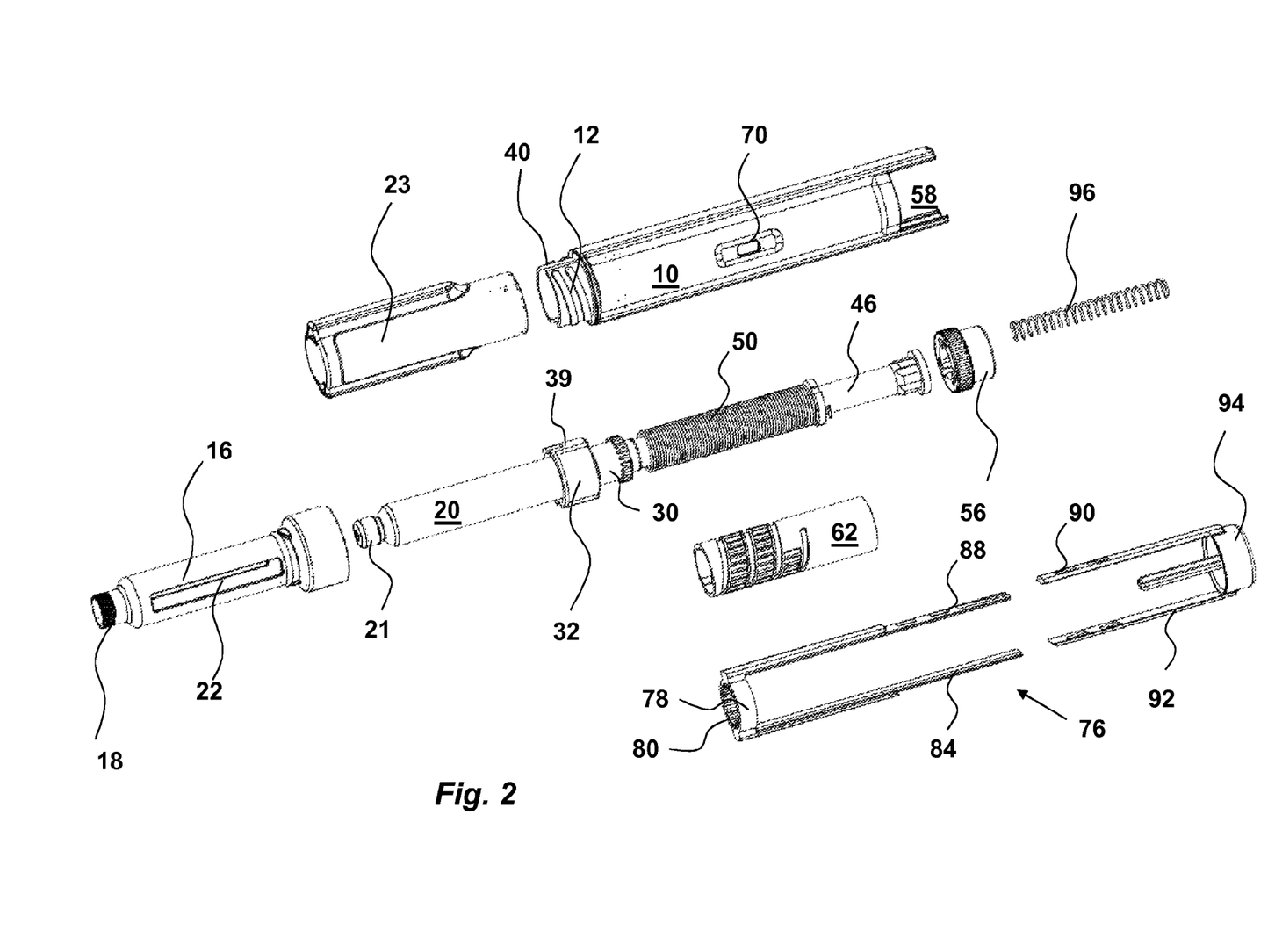
FIG. 2 is an exploded view of the device of FIG. 1.
Figure 3:
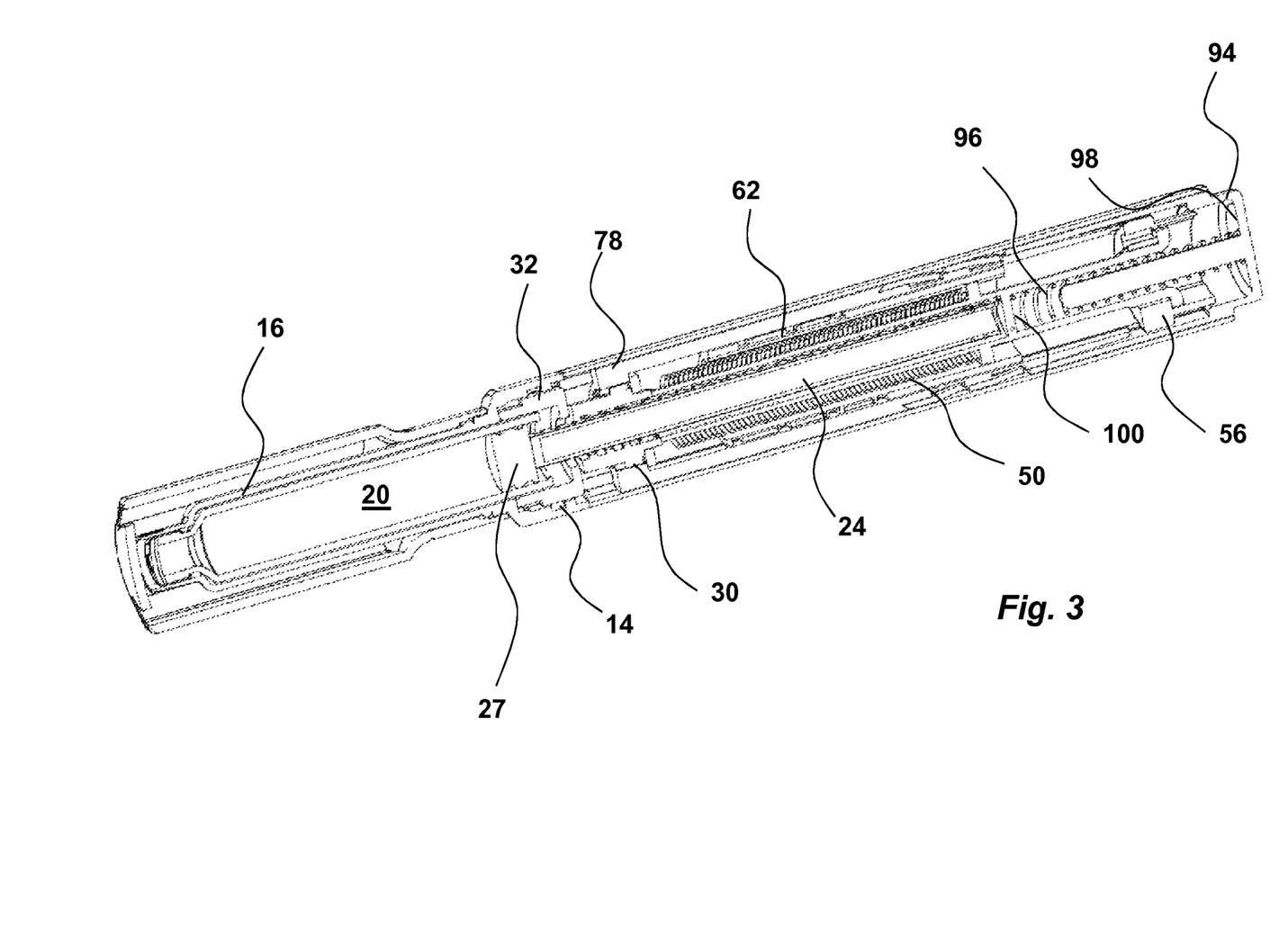
FIG. 3 is a cross-sectional view of the device of FIG. 1.
Figure 4:
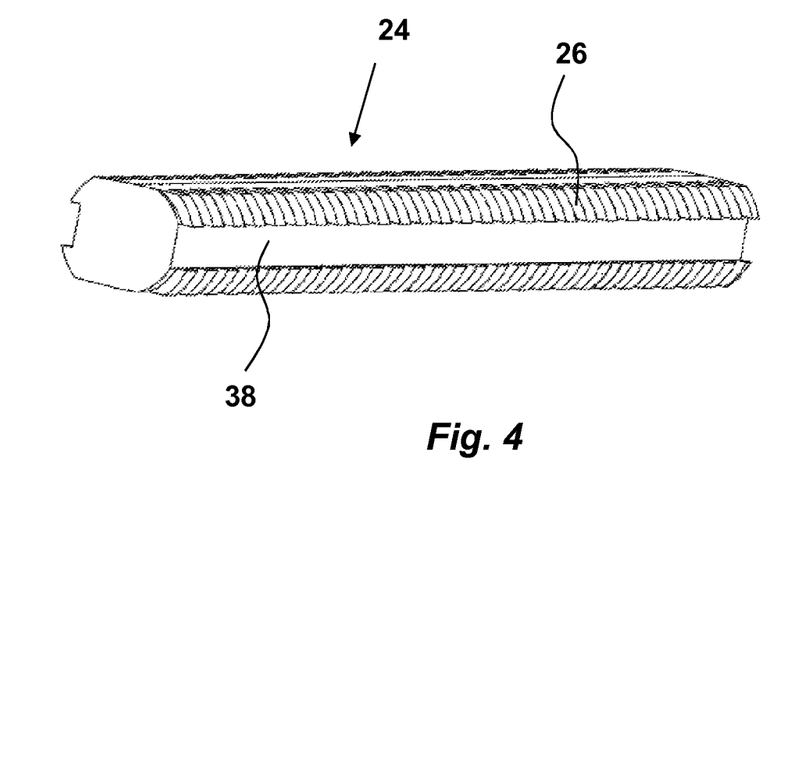
FIG. 4 is a detailed view of a guide member and plunger rod comprised in the device of FIG. 1.

The device further comprises a drive unit 25, which in turn comprises a generally elongated plunger rod 24 arranged to act on a stopper 27, FIG. 3, movably arranged inside the medicament container 20. The plunger rod 24 is arranged with threads 26 on its outer surfaces, which threads 26 cooperate with corresponding threads 28 of a drive nut 30, FIG. 5, of the drive unit 25. Further a guide member 32, FIG. 4, is arranged surrounding the plunger rod 24, which guide member 32 is arranged with a central passage 34 having inwardly extending protrusions 36 fitting into elongated grooves 38 of the plunger rod 24, enabling a rotational lock between the two. Further the guide member 32 is arranged with ledges 39 on its outer surface fitting into cut-outs 40, FIG. 2, on the proximal end of the distal housing part 10, whereby the guide member 32 is rotationally locked in relation to the distal housing part 10 when the proximal 16 and distal 10 housing parts are connected to each other.

Figure 5:
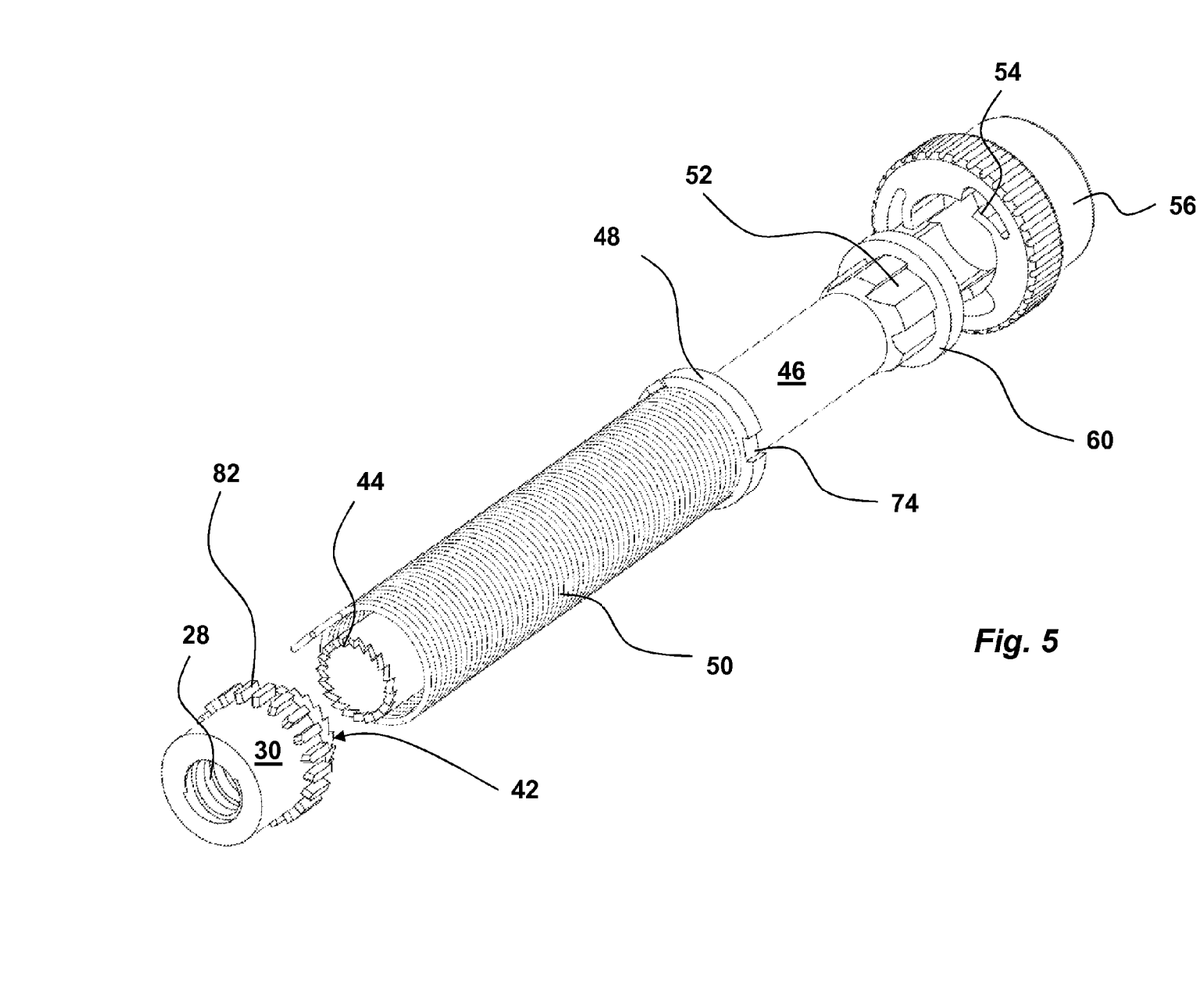
FIG. 5 is a detailed view of a drive unit comprised in the device of FIG. 1.

The distal end of the drive nut 30 is arranged with a wedge-shaped circumferential ratchet 42, FIG. 5, which is arranged to cooperate with a corresponding proximally directed wedge-shaped ratchet 44 of a drive member 46 comprised in the drive unit 25. The drive member 46 is generally tubular and surrounds the plunger rod 24. On its outer surface a circumferentially extending ledge 48 is arranged, FIG. 5. Further a torsion drive spring 50, comprised in the drive unit, is arranged around said drive member 46 having a distal end attached to said ledge 48. The proximal end of the torsion drive spring 50 is attached to the housing. At the distal end of the drive member 46 a number of wedge-shaped ledges 52 are arranged around the circumference. These ledges 52 are arranged to cooperate with radially flexible arms 54 arranged on an inner surface of a dose setting button 56, which button 56 is arranged rotatable in said housing and accessible via cut-outs 58, FIG. 2, in the housing. The dose setting button 56 is held in the longitudinal direction by a circumferential ledge 60, FIG. 5, at the distal end of the drive member 46.

Figure 6:
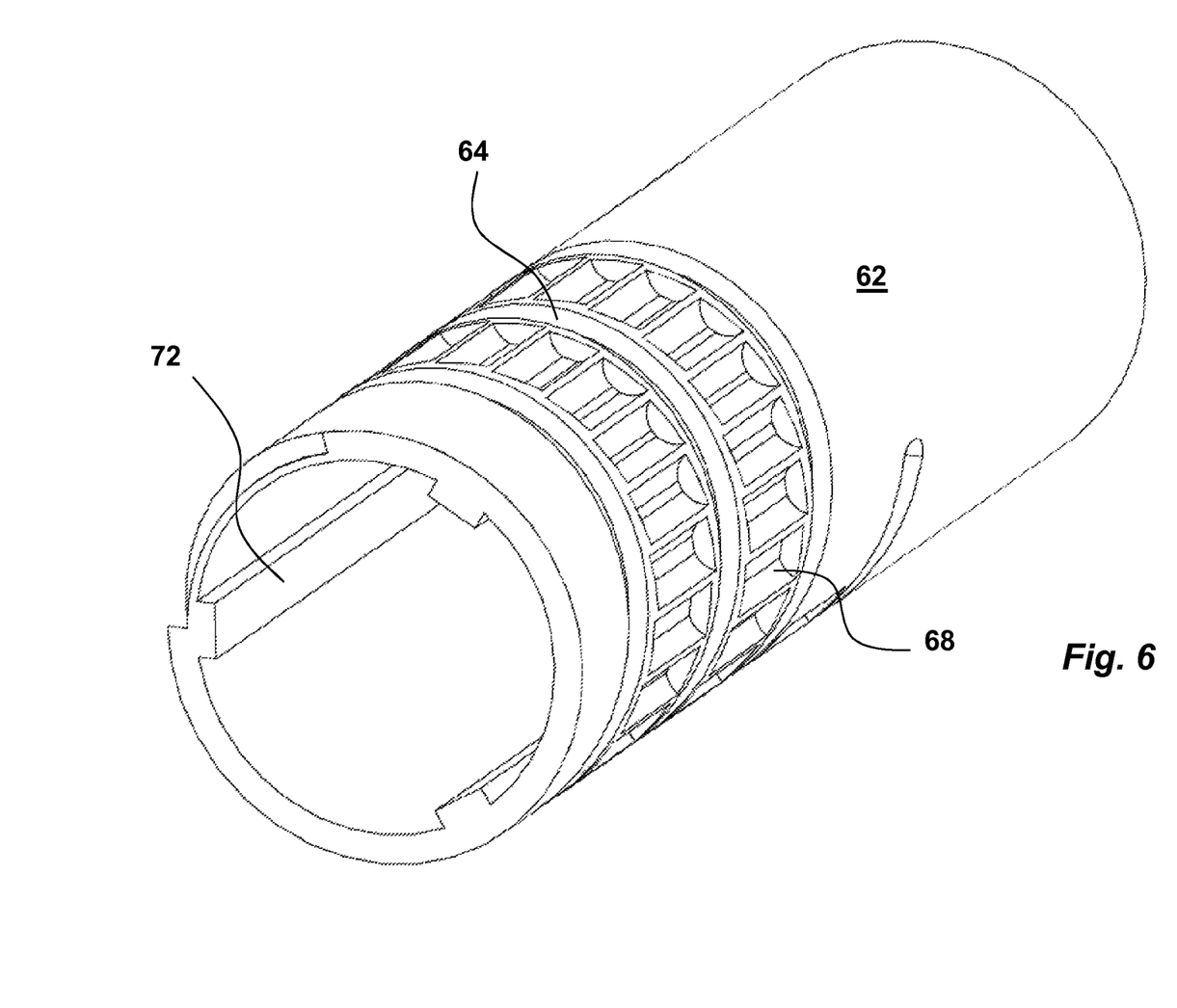
FIG. 6 is a detailed view of a dose barrel comprised in the device of FIG. 1.
Figure 7:
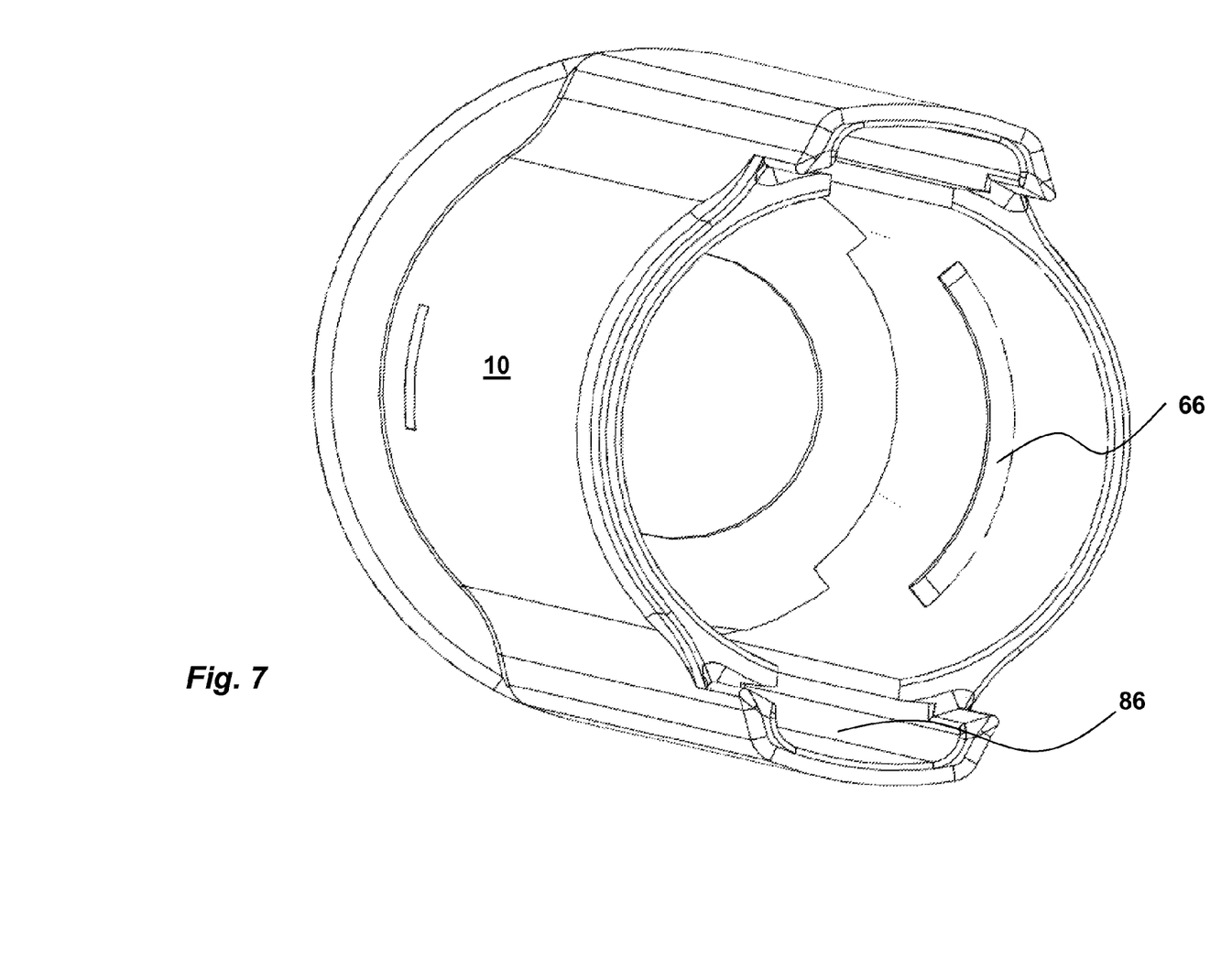
FIG. 7 is a detailed view of a distal housing part comprised in the device of FIG. 1, FIGS. 8 & 9 show functional positions of the device of FIG. 1 with certain components removed for clarity.

Surrounding the drive member 46 and the torsion drive spring 50 of the drive unit 25 is a generally tubular dose barrel 62, FIG. 6. The dose barrel 62 is arranged with a spirally extending groove 64 on its outer surface, which spiral groove 64 cooperates with an inclined ledge 66 on the inner surface of the distal housing part 10, FIG. 7. The outer surface of the dose barrel 62 is further arranged with indicia 68 positioned in a spiral pattern, which indicia 68 are visible in a window 70, FIG. 2 on the distal housing part 10. The inner surface of the dose barrel 62 is arranged with longitudinally extending ledges 72, FIG. 6, which ledges 72 fit into cut-outs 74, FIG. 5, on the circumferential ledge 48 of the drive member 46 so as to lock the dose barrel 62 rotationally but allow linear movement in the longitudinal direction.

The device also comprises an activation mechanism 76, FIG. 2, which comprises a ring-shaped drive nut lock member 78 having locking members in the form of splines 80 on its inner surface, which splines 80 are designed to cooperate with longitudinally extending ledges 82, FIG. 5, around the outer surface of the drive nut 30. To the drive nut locking member 78 of the activation mechanism, two arms 84, FIG. 2, are attached, which arms 84 form actuation members and extend in longitudinally extending grooves 86, FIG. 7, on the inner surface of the distal housing part 10. The arms 84 are arranged with attachment means 88 that are arranged to cooperate with corresponding attachment means 90 on two proximally directed arms 92, which arms 92 are attached to an activation button 94, which button 94 is protruding through a distal opening in the distal housing part. A spring 96, FIG. 3, is arranged between a proximally directed end wall 98 of the activation button 94 and an interior wall 100, FIG. 3, of the drive member 46 for urging the activation button 94 in the distal direction.

The device is intended to function as follows. When delivered to a user, the device could either be ready for use with a medicament container 20 already installed in the proximal housing part 16 or it is delivered with the medicament container 20 delivered separately. In the latter case the user disconnects the proximal and distal housing parts, introduces the medicament container and re-connects the housing parts.

Figure 8:
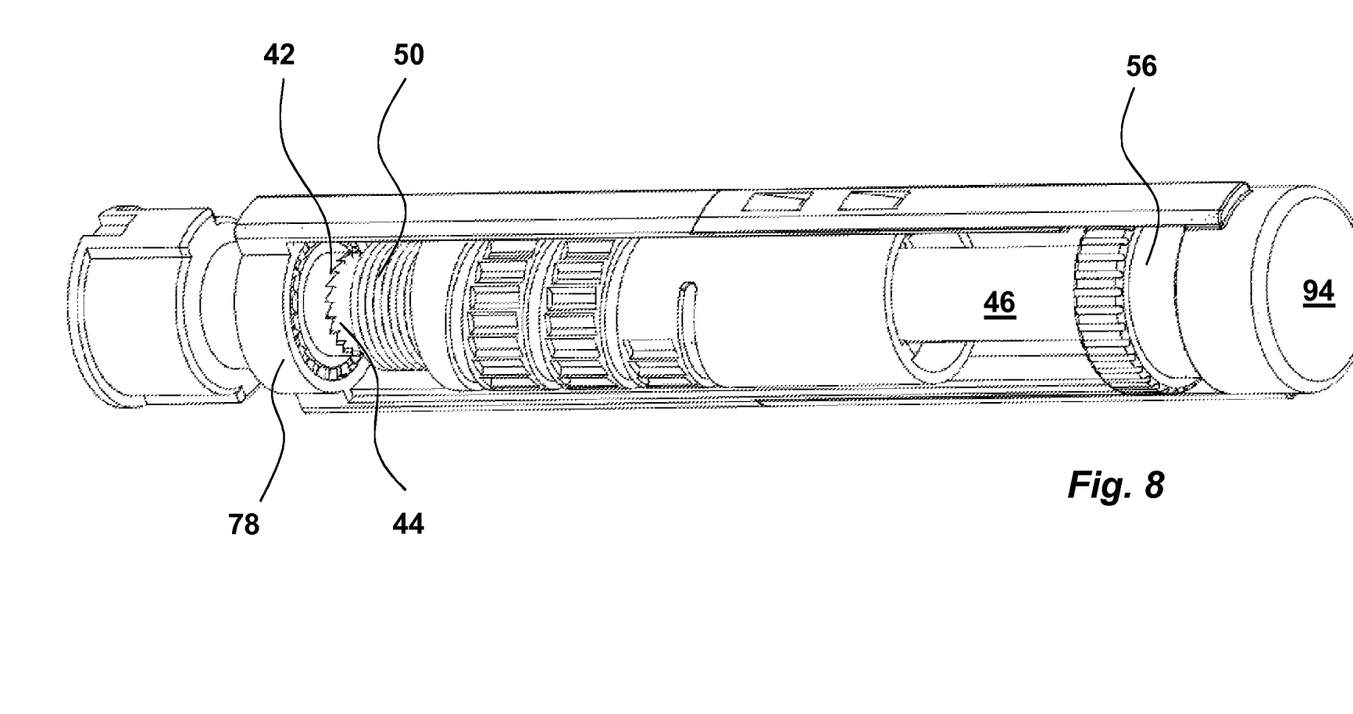

When a dose of medicament is to be delivered the protective cover 23 is removed and a medicament delivery member is attached to the neck portion 18 of the proximal housing part. The next step is then to set a dose of medicament to be delivered. This is done by turning the dose setting button 56 a certain angular distance. This turning causes also the drive member 46 to be turned due to the arms 54 of the dose setting button 56 acting on the wedge-shaped ledges 52 of the drive member 46. The turning of the drive member 46 causes in turn the torsion spring 50 to be tensioned due to its attachment to the ledge 48 of the drive member 46. The ratchet 44 of the drive member 46 will slide over the ratchet 42 of the drive nut 30 and the latter will be held stationary by the locking members, i.e. the splines 80 of the drive nut locking member 78 engaging the ledges 82 of the drive nut 30, FIG. 8. Further, the dose barrel 62 will also rotate due to the connection with the ledges 72 positioned in the cut-outs 74 in the ledge 48 of the drive member 46. The rotation of the dose barrel 62 will cause it to move in the distal direction due to its spiral groove 64 cooperating with the ledge 66 of the inner surface of the distal housing part 10. During rotation of the dose barrel, indicia 68 will pass the window until the appropriate dose is displayed in the window.

Should the user accidentally have set a dose larger than the prescribed dose, the user can grip the dose setting button 56 and pull it in the distal direction against the force of the spring 96. For this purpose the cut-outs 58 in the distal housing part 10 are made so large as to admit this. The distal end surface of the dose setting button will then be in contact with the ledge 60 at the distal end of the drive member 46, whereby the drive member 46 will also be moved in the distal direction. This causes the ratchet 44 of the drive member 46 to move out of contact with the ratchet 42 of the drive nut, whereby it is possible to turn back the dose setting button 56, the drive member 46 and the dose barrel 62.

Figure 9:
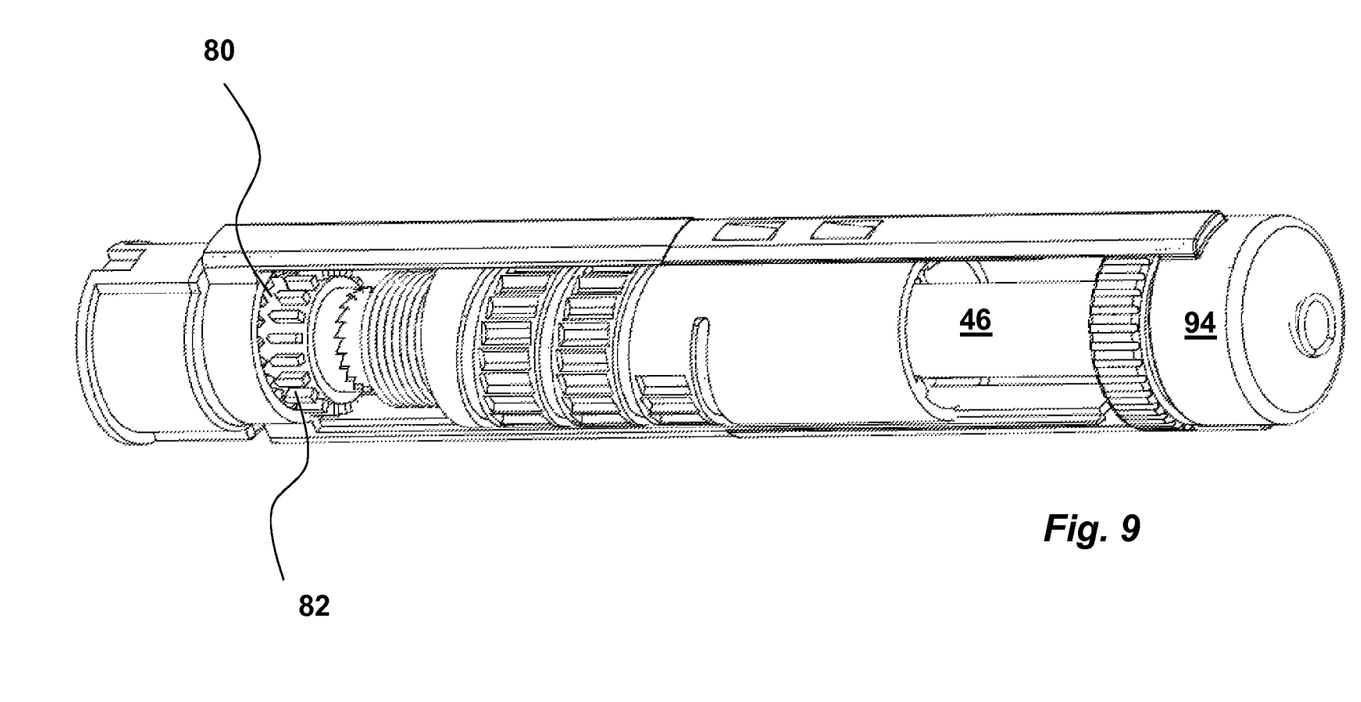

When now the dose has been set, the next is to deliver the set dose. The proximal end of the device with the medicament delivery member is then positioned at the dose delivery site. Then the activation button 94 is pressed in the proximal direction by the user. This also causes the locking member 78 with its splines 80 to move in the proximal direction by the arms 84, 92 such that the splines 80 are moved out of contact with the ledges 82 of the drive nut 30, FIG. 9. Now the drive nut 30 is free to rotate and will do so due to the locked connection between the ratchets 42, 44 and due to the spring force of the torsion spring 50 acting on the drive member 46. The rotation of the drive nut 30 will now cause the plunger rod 24 to move in the proximal direction due to the threads 28 of the drive nut 30 acting on the threads 26 of the plunger rod 24 and due to the rotationally locked connection between the plunger rod 24 and the guide member 32 due to the protrusions 36 fitting into the grooves 38. The movement of the plunger rod 24 causes the stopper 27 to be moved in the proximal direction inside the medicament container 20, causing a dose of medicament to be expelled through the medicament delivery member. Further the rotation of the drive member 46 will cause the dose barrel 62 to rotate back to the initial position, indicated by e.g. "0".

Also, in order to reduce the risk that the user is preventing rotation of the dose setting button 56, the drive member 46 and the drive nut 30, i.e. preventing a dose delivery if he/she is gripping the device such that the hand is in contact with the dose setting button 56, the drive member 46 and thus the drive nut are free to rotate back because the flexible arms 54 of the dose setting button 56 now slide over the wedge-shaped ledges 52 of the drive member 46, FIG. 5.

The above dose setting and dose delivery procedure is repeated for a number of doses, preferably with a new sterile medicament delivery member for each dose, until the medicament container is emptied. The empty medicament container can now be replaced by a new container by disconnecting the proximal housing part 16 from the distal housing part 10. It is further possible to rotate back the plunger rod in its initial position because the guide member 32 is no longer locked by the housing parts.

It is to be understood that the embodiment described above and shown in the drawings is to be regarded only as a non-limiting example of the invention and that it may be modified in a number of ways within the scope of the patent claims.

The invention claimed is:

1. A medicament delivery device, comprising:
 a housing having at least one housing part and configured to receive a medicament container;
 a driver configured to act on a stopper in the medicament container and comprising a torsion drive spring;
 a dose setting member operably connected to the driver such that manually turning the dose setting member causes a tensioning of the torsion drive spring; and
 an activation mechanism having an activation button protruding through a distal end of the medicament delivery device and being operably connected to the driver such that actuation of the activation mechanism releases the driver, whereby a set dose of medicament is delivered;
 wherein the driver further comprises:
  an elongated plunger rod extending in a longitudinal direction of the medicament delivery device, the plunger rod having threads on its outer surface and a proximal end in contact with the stopper;
  a drive nut having a central passage with threads that cooperate with the threads of the plunger rod; and
  a drive member having a proximal end operably engaging the drive nut and drivably connected to the torsion drive spring such that, upon actuation of the activation mechanism, the drive nut and drive member are rotated, whereby the plunger rod is moved in a proximal direction of the medicament delivery device;
 and the activation mechanism comprises actuation members attached to the activation button and extending in the proximal direction of the medicament delivery device, a drive nut lock member attached to the actuation members and releasably engaging and locking the drive nut via cooperating locking members until the actuation button is moved in the proximal direction, whereby the drive nut is released.

2. The medicament delivery device of claim 1, wherein the drive nut and drive member are operably connected via wedge-shaped ratchets configured to enable turning of the drive nut when the drive member is turned by the torsion drive spring upon activation, thereby driving the plunger rod for expelling a dose of medicament from the medicament container, and configured such that the dose setting member is operably connected to the drive member such that manual operation of the dose setting member causes a turning of the drive member in relation to the drive nut for setting a dose of medicament to be delivered from the medicament container and tensioning the torsion drive spring.

3. The medicament delivery device of claim 1, further comprising a dose barrel rotatably arranged inside the housing and operably connected to the dose setting member, wherein the dose barrel includes indicia on its outer surface visible in a window in the housing, and the indicia display a set dose when the dose setting member is turned by a user.

4. The medicament delivery device of claim 3, wherein the dose barrel includes threads on its outer surface that cooperate with corresponding threads on an inner surface of the housing.

5. The medicament delivery device of claim 4, wherein the indicia are positioned spirally on the dose barrel.

6. The medicament delivery device of claim 2, wherein the dose setting member and the drive member are axially movable in a distal direction against a force from a spring such that displacement of the dose setting member in the distal direction causes the ratchets to move out of contact with each other, thereby enabling resetting of a set dose.

7. The medicament delivery device of claim 1, wherein the housing comprises a distal part and a proximal part, the proximal part is arranged to accommodate the medicament container, and the distal and proximal parts include releasable attachment devices.

8. The medicament delivery device of claim 7, further comprising a guide member configured to rotatably lock the plunger rod, wherein the attachment devices act on and lock the guide member when the distal and proximal parts are attached to each other, and when the distal and proximal parts are disconnected from each other, the guide member and plunger rod are freed, whereby the plunger rod can be moved in the distal direction to an initial position for a new medicament container to be used.

9. A medicament delivery device, comprising:
 a housing having at least one housing part and configured to receive a medicament container;
 a driver configured to act on a stopper in the medicament container and comprising a torsion drive spring;
 a dose setting member operably connected to the driver such that manually turning the dose setting member causes a tensioning of the torsion drive spring;
 an activation mechanism having an activation button protruding through a distal end of the medicament delivery device and being operably connected to the driver such that actuation of the activation mechanism releases the driver, whereby a set dose of medicament is delivered; and
 a dose barrel rotatably arranged inside the housing and operably connected to the dose setting member, wherein the dose barrel includes indicia on its outer surface visible in a window in the housing, and the indicia display a set dose when the dose setting member is turned by a user.

10. The medicament delivery device of claim 9, wherein the dose barrel includes threads on its outer surface that cooperate with corresponding threads on an inner surface of the housing.

11. The medicament delivery device of claim 10, wherein the indicia are positioned spirally on the dose barrel.

* * * * *